United States Patent [19]

Nayar et al.

[11] Patent Number: 4,988,202
[45] Date of Patent: Jan. 29, 1991

[54] SOLDER JOINT INSPECTION SYSTEM AND METHOD

[75] Inventors: Shree K. Nayar, Pittsburgh, Pa.; Arthur C. Sanderson, Williamstown, Mass.; Lee E. Weiss; David A. Simon, both of Pittsburgh, Pa.

[73] Assignee: Westinghouse Electric Corp., Pittsburgh, Pa.

[21] Appl. No.: 372,481

[22] Filed: Jun. 28, 1989

[51] Int. Cl.$^5$ ............................................. G01B 11/24
[52] U.S. Cl. .................................. 356/394; 250/560; 356/376; 358/101; 358/106
[58] Field of Search ................... 356/376, 394, 237; 358/101, 106, 107; 250/560

[56] References Cited

U.S. PATENT DOCUMENTS

| | | | |
|---|---|---|---|
| 3,976,382 | 8/1976 | Westby | 356/120 |
| 4,185,918 | 1/1980 | DiMatteo et al. | 356/375 |
| 4,238,147 | 12/1980 | Stern | 354/77 |
| 4,427,880 | 1/1984 | Kanade et al. | 250/222.1 |
| 4,452,534 | 6/1984 | Gribanov et al. | 356/359 |
| 4,472,056 | 9/1984 | Nakagawa et al. | 356/376 |
| 4,473,750 | 9/1984 | Oshida et al. | 250/560 |
| 4,508,452 | 4/1985 | DiMatteo et al. | 356/375 |
| 4,634,879 | 1/1987 | Penney | 250/560 |
| 4,650,333 | 3/1987 | Crabb et al. | 356/376 |
| 4,657,393 | 4/1987 | Stern | 356/376 |
| 4,677,473 | 6/1987 | Okamoto et al. | 358/101 |
| 4,695,163 | 9/1987 | Schachar | 356/369 |
| 4,748,335 | 5/1988 | Lindow et al. | 250/572 |
| 4,791,482 | 12/1988 | Barry et al. | 358/107 |
| 4,876,455 | 10/1989 | Sanderson et al. | 356/376 |

Primary Examiner—F. L. Evans
Attorney, Agent, or Firm—J. G. Porcelli

[57] ABSTRACT

The invention is an automated solder joint inspection system for determining the quality of a specular soldered joint through examination of the shape of the joint surface using a series of point light sources and the associated highlight reflections from the joint surface. The light from point light sources, which is directed toward the solder joint, is reflected in a pattern from the solder joint to an array of light responsive transducers from at least one location. Utilizing the intensity values from the light responsive transducer array, the surface orientation of the solder joint at a number of points is determined. The solder joint is evaluated in one of two ways. In one way, using known surface features of solder joints along with curve fitting techniques, a series of grid maps is mathematically interpreted to reconstruct the solder joint surface. A rule-based system, through comparison with acceptable solder joint surface features, evaluates and classifies the joint for an acceptability determination. In another way the surface orientation is used to generate an Extended Gaussian Image of the joint and the features of this are analyzed.

16 Claims, 9 Drawing Sheets

SOLDER JOINT INSPECTION SYSTEM AND METHOD

CROSS-REFERENCE TO RELATED APPLICATION

This application is related to pending U.S. patent application Ser. No. 07/160,562 filed Feb. 25, 1988 entitled SOLDER JOINT INSPECTION SYSTEM. This application is also related to pending U.S. patent application Ser. No. 07/313,212 filed Feb. 21, 1989, entitled A DEVICE FOR EXTRACTING SHAPE AND REFLECTANCE OF THREE DIMENSIONAL SURFACES.

FIELD OF THE INVENTION

This invention is directed to a solder joint inspection system and method and more particularly to a system and method which provide a non-contact inspection of solder joints having specular surfaces.

BACKGROUND OF THE INVENTION

Automated inspection of solder joints, especially those used on printed circuit boards, has become increasingly important with the proliferation of automatic electronic assembly technology. Human visual inspection is becoming less cost effective and more unreliable because of the time consuming microscopic inspection required for the typically thousands of solder joints per board. A primary feature of solder joint quality is the shape of the joint surface. Therefore the ability to automate the measurement of solder joint shapes and detect defects through shape is a significant requirement of a fully automated system. Current progress toward automated inspection includes development of optical non-contact inspection systems capable of very accurate measurements but these systems are fairly complex.

The pending patent application referenced in the CROSS-REFERENCE TO RELATED APPLICATION section entitled SOLDER JOINT INSPECTION SYSTEM addresses an optical system for determining the orientation of a number of points on the surface of a specular object, such as a solder joint, and utilizing known surface features of the object along with the known orientations to approximately reconstruct the shape of the object.

The pending patent application referenced in the CROSS-REFERENCE TO RELATED APPLICATION section entitled A DEVICE FOR EXTRACTING SHAPE AND REFLECTANCE OF THREE DIMENSIONAL SURFACES addresses an optical system for object surface shape and reflectance extraction utilizing extended light sources, not point light sources.

U.S. Pat. No. 4,695,163 issued on Sept. 22, 1987 to Ronald A. Schachar entitled "Method and Apparatus for Determining Surface Shapes Using Reflected Laser Light" discloses a method and apparatus for determining the surface shape of an object by scanning the object with a light beam incrementally movable in a linear and angular direction. The light beam must be physically moved and directed across the surface of the object a number of times and at a multitude of angles so that light detectors may provide adequate accurate information for a determination of the surface shape. Using light beams which cover only a portion at a time of the object to be inspected, this method and apparatus provides precise information to determine surface orientations but becomes cumbersome when only an approximate profile is desired.

U.S. Pat. No. 4,508,452 issued on Apr. 2, 1985 to Paul L. DiMatteo, Joseph A. Ross, and Howard K. Stern entitled "Arrangement for Sensing the Characteristic of a Surface and Determining the Position of Points Thereon" discloses a method and arrangement for optical inspection utilizing a projector illuminating a series of predetermined sections on an object and simultaneously a camera moving about the object taking multiple photographs for subsequent analysis. The entire surface of the object is inspected and accurately mapped. No prior knowledge of the shape of the object is needed for this approach.

U.S. Pat. No. 4,427,880 issued on Jan. 24, 1984 to Takeo Kanade and Haruhiko Asada entitled "Non-Contact Visual Proximity Sensing Apparatus" teaches an apparatus for determining the location and orientation of an object utilizing a plurality of light sources spaced apart in a pattern. The light sources are directed at a symmetrical object and the reflected beams impinge on the surface of a light sensitive transducer. The pattern of these reflected beams is then analyzed to determine the location and relative orientation of the object. Note this technique does not reveal any details about the surface geometry but only the orientations and locations of an object whose geometry is already known.

U.S. Pat. No. 4,791,482 issued on Dec. 13, 1988 to Robert F. Barry and Samuel Kang entitled "Object Locating System" teaches the generation of Gaussian images for comparison between reference objects and objects to be identified. See column 7, line through column 8, line 22.

FIG. 1A shows one lead 10 from a typical surface mounted flatpack semiconductor chip 11 attached with solder shown generally by 12 to a solder pad 13 on a printed circuit board 14. FIG. 1B shows the top view of this arrangement while FIG. 1C shows a cross-section view "1C—1C". For assessment of the quality of the solder joint 12 for a flatpack chip 11, the relevant part of the lead 10 for inspection is the underside of the foot 15 portion of the lead 10. Because the foot 15 is positioned flat on the solder pad 13, a small amount of solder is sufficient to make a proper connection between the foot 15 and the solder pad 13. Note the meniscus 16 of solder that has been displaced from under the foot 15 to the sides and back of the foot 15. The portion of the meniscus 16 to the front of the foot 15 is the toe 17. The portion to the sides is the shoulder 18, while that portion of the meniscus to the rear of the foot 15 is the heel fillet 19. The wetting of the lead can be assessed at its true worth from the solder meniscus, however small, at all four sides of the foot 15. Further requirements on the amount of solder for flatpacks is usually not necessary. Note that further information on the assessment of solder joints may be found in "Soldering in Electronics" by R. J. Klein Wassink. FIG. 1C highlights critical features of a typical solder joint such as the toe 17, the shoulder 18, and the heel fillet 19 on a lead 10 of a surface mounted chip 11 on a printed circuit board 14. Note again the most critical solder is not apparent with visual inspection because it occurs between the bottom of the foot 15 and the top of the solder pad 13. The meniscus shown by the toe 17, shoulder 18, and heel fillet 19 is indicative of the quality of that unseen solder joint. By examining the shape of the solder meniscus and comparing this to known acceptable shapes, it is possible to determine the acceptability of the solder joint. Typically, in order to determine the acceptability of a solder joint, the shape of the joint is determined and that shape compared with the shapes of acceptable solder joints. Because a large multitude of shapes may be acceptable shapes, this approach becomes fairly involved and cumbersome.

It is the object of this invention to provide a method and system for determining profile information of solder joints, utilizing reflections from their specular surfaces. Using optical scanning along the surface of a solder joint, it is desired to generate a profile approximating that of the solder joint.

Another object of the present invention is to provide an improved method and system for surface profile determination of solder joints using a selective optical sensing such that safe, low power optical sources may be used.

Another object of the present invention is to reduce the number of data points required to determine the surface geometry of the solder joint by utilizing a priori knowledge about the salient features of the solder joint to predict the behavior of the surface in regions where data was not acquired.

Yet another object of the present invention is to compare the surface features of the object, i.e. solder joint, with typical solder joint surface features to determine joint integrity because the shape of the solder joint reveals the quality of the joint.

Still another object of the present invention is to provide a method for evaluating the solder joint based solely on the surface features of the joint such that joint reconstruction is unnecessary.

SUMMARY OF THE INVENTION

The invention is an automated solder joint inspection system for determining the quality of a specular soldered joint through examination of the shape of the joint surface using a series of point light sources and the associated highlight reflections from the joint surface. The light from the point light sources, which is directed toward the solder joint, is reflected in a pattern from the solder joint to an array of light responsive transducers, such as a camera, from at least one fixed location. Utilizing the intensity values from the light responsive transducer array, a binary grid map is generated for the reflections from each point light source. In one embodiment using known surface features of solder joints along with curve fitting techniques, a series of grid maps may be mathematically interpreted to reconstruct the solder joint surface. A rule-based system, through comparison with acceptable solder joint surface features, evaluates and classifies the joint for an acceptability determination. In a second embodiment the surface reflections of the joint are utilized to generate an Extended Gaussian Image representation of the joint which is then evaluated to determine the joint acceptability.

BRIEF DESCRIPTION OF THE DRAWINGS

The above as well as other features and advantages of this system will become apparent through consideration of the detailed descriptions in connection with the accompanying drawings in which.

DESCRIPTION OF THE PREFERRED EMBODIMENT

The inspection system in this application is based on two concepts. First, as it turns out, the surface of a solder joint is specular, that is, having a surface that ideally reflects light only at an angle of reflection equal to the angle of incidence. Consequently for highly specular surfaces such as solder joints, a bright spot of detectable intensity can be seen on the surface only if the viewing angle is the angle of reflection. This surface is contrasted to a Lambertian surface which appears equally bright from all viewing directions and reflects all incident light. A typical example of a specular surface would be a surface plated with chrome while an example of a Lambertian surface would be the surface of a piece of tissue paper. Second the features of acceptable and unacceptable solder joints are well known. This is important not only because the solder joint quality may be determined by the joint shape but also because to determine the shape of a solder joint, it is not necessary to examine the entire surface of the joint. Only enough data points are required so that critical features of the joint are revealed. This information may be used to reconstruct the solder joint for comparison with acceptable solder joint shapes or the information by itself may be analyzed through such a method as mapping upon an Extended Gaussian Image and evaluated for a determination of solder joint quality. For solder joint reconstruction, curve fitting techniques coupled with knowledge of solder joint profiles may be used to adequately overcome a deficiency that may be caused by a lack of data points.

Figure 2A:
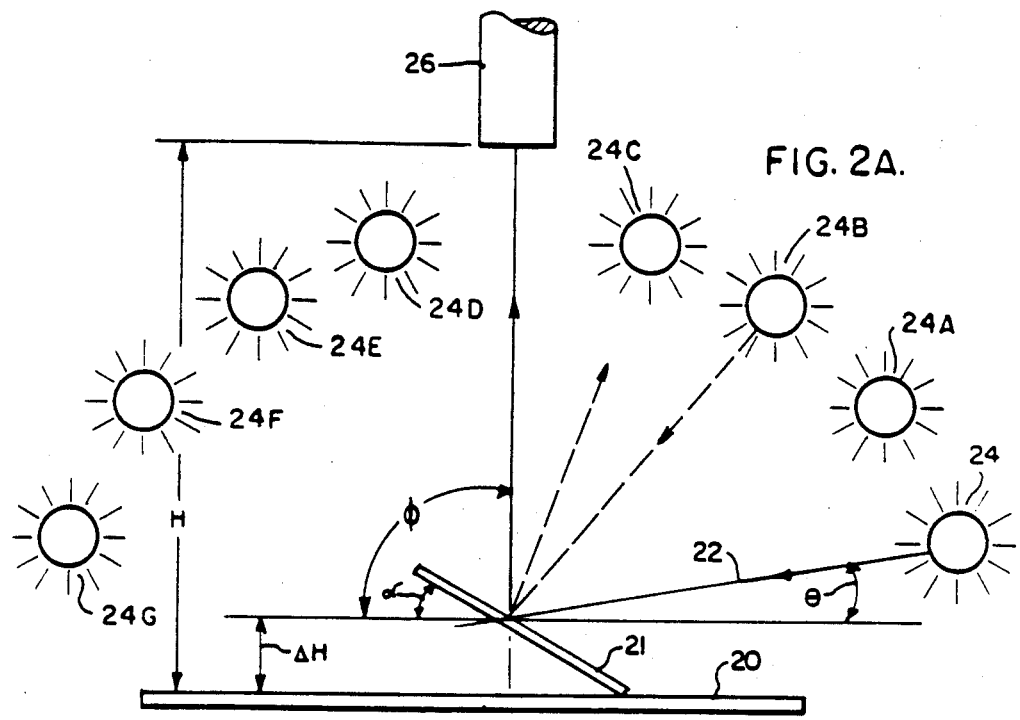
FIGS. 2A and 2B are illustrations showing the method used for determination of the surface orientation at a point on a specular surface.
Figure 2B:
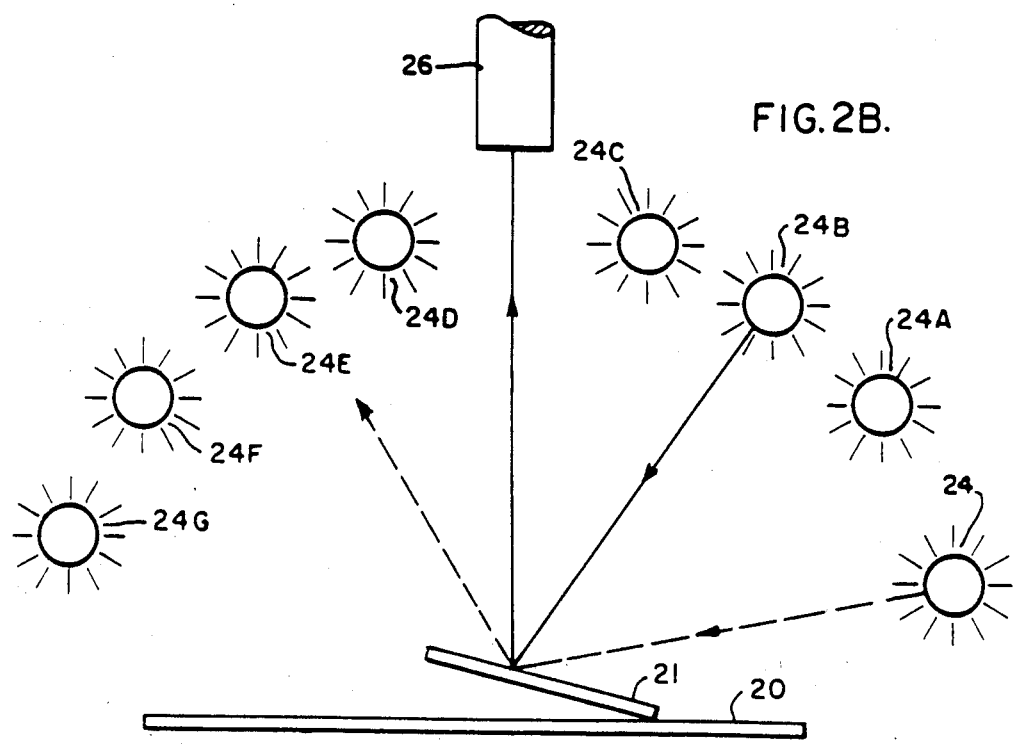

FIG. 2A shows a sketch from which the theory for the method used in determining the orientation of a surface at one point may be presented. A reference plane 20 is defined as the surface on which the object of interest 21 sits. For the application under consideration, the reference plane 20 is a printed circuit board and the object of interest 21 is the solder joint. For clarity the object of interest 21 is shown to be planar; however, this is merely for use as an example. A typical object for inspection would have a non-planar shape and the object could be broken into a finite number of small planar elements. It is one of these small planar elements which is exaggerated in size to form the object of interest 21 shown in FIG. 2A. A light point source 24 is located at a known angle $\theta$ from the object of interest 21 such that a light ray 22 striking the object of interest 21 is reflected to a series of light sensitive transducers such as those in a solid state camera 26. The camera is in a fixed location and is directed toward the object of interest 21 from a single direction. The camera does not have the capability to move either in translation or rotation. Note that the orientation of the object of interest 21 in FIG. 2A is such that point light source 24 provides a light ray that is reflected from the object 21 to the camera 26. However, a point light source 24B provides a light ray that does not reflect from the object 21 to the camera 26. As shown in FIG. 2B, if the object 21 were oriented differently, then the point light source 24B would provide a light beam that would be reflected to the camera 26. In this manner the series of light point sources 24 and 24A-24G can be used to detect a variety of surface orientations that may exist on an object. Note also in FIG. 2A the camera 26 is positioned at a known distance, H, from the reference plane 20 and H is the highest point on the object from the reference plane 20. If H is much greater than $\Delta H$, then an assumption may be made that all points on the object lie on the reference plane 20. This is a key assumption because now given angle $\theta$ of the point light source 24 in FIG. 2A relative to the reference plane 20 at the object of interest 21 and angle $\phi$ between the line of sight of the camera 26 and the reference plane 20, knowing that the angle of incidence for the light ray 22 is equal to the angle of reflectance, the angle $\alpha$ of the object of interest 21 relative to the reference plane 20 may be calculated. An angle normal to the face of the object 21 from which light rays are reflected may then be determined. By providing a plurality of point light sources 24A-24G at locations other than that for point light source 24, with each point light source directed toward the object 21 similar information on local surface orientations over the face of the object 21 which would have a variety of surface orientations may be collected.

Given the local surface orientation of many points on the object then either the entire surface of the object can be reconstructed for analysis, with gaps filled in using curve fitting techniques, or the local surface orientations in themselves may be analyzed in some manner, such as through generating an Extended Gaussian Image of the object based on surface orientation for evaluation.

Figure 3:
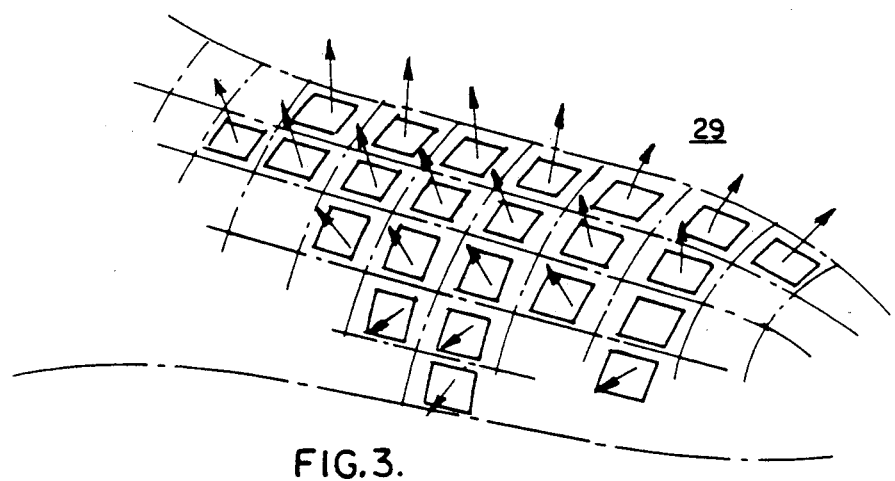
FIG. 3 is an illustration of a three dimensional reconstruction of a solder joint utilizing data from a finite number of points showing surface orientation.

FIG. 3 shows a three dimensional reconstruction 29 of a solder joint made with knowledge of only a limited number of data points. Generally the shape of a solder joint is a continuous surface and because of this the lack of closely spaced data points across the entire surface is not critical. The gaps may be filled using general knowledge of solder joint shapes.

Figure 4:
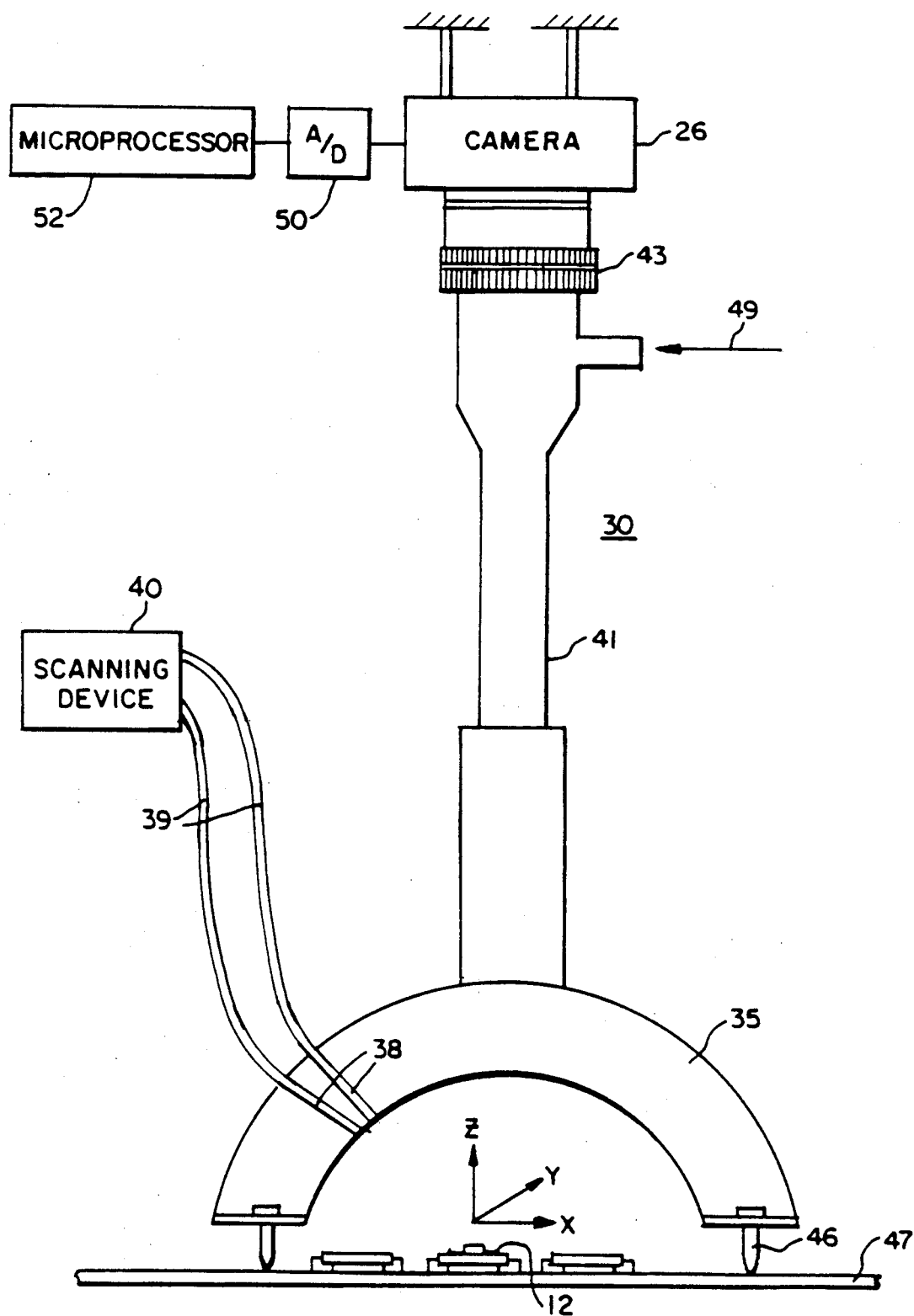
FIG. 4 is an illustration of the inspection apparatus for the determination of the solder joint surface orientation.

An embodiment of the inspection system is shown in FIG. 4. A camera 26 is supported by a structural frame (not shown) and the remainder of the system is supported by the camera 26. The camera 26, using the structural housing of an imaging device 30, supports a fixed arcuate two-dimensional configuration in the form of a semicircular frame 35. The semicircular frame 35 functions to configure an array of point light sources such that the point light sources are directed toward the object of interest, which is a solder joint 12, using a plurality of equally spaced radially located penetrations 38 extending from the outer diameter wall to the inner diameter wall of the frame 35. Optical fibers 39 transmit the light from at least one light source within a scanning device to generate a series of point light sources. While only two fibers 39 are shown in FIG. 4, these are representative of fibers located over the entire arc of the frame 35. Optical fibers 39 pass through penetrations 38 and are thereby oriented such that a point light source through any fiber will illuminate the surface of the solder joint 12. An opening exists through the semicircular frame 35 and the imaging device 30 so that the camera 26 has an unobscured line of sight to the object of interest, which is the solder joint 12, or it may be controlled entirely with electronic circuitry whereby the option exists to illuminate one fiber 39 at a time or illuminate simultaneously any series of fibers.

While one end of each optical fiber 39 is connected radially to the frame 35, the other end of each fiber 39 is attached to a singular scanning device 40. The singular scanning device 40 may be either an electromechanical or electronic scanner capable of illuminating one fiber 39 at a time, or it may be controlled entirely with electronic circuitry whereby the option exists to illuminate one fiber 39 at a time or illuminate simultaneously any series of fibers. The device 40 provides a means for selecting a particular fiber 39 and guiding a light beam into that fiber 39 and also provides a means for sequentially directing the light source to each fiber 39 to generate individual point light sources. Also, as indicated, the device 40 may provide a means for sequentially directing the light source to each of a set of fibers to generate multiple point light sources. As will be explained, while illuminating a single point light source at a time does provide adequate information for analysis, the speed of the entire scanning process may be increased utilizing a binary coding technique, and it is this technique that requires the illumination of more than one point light source at one time. Use of a scanning device 40 provides a distinct advantage over some systems that utilize a singular point light source which is mechanically moved from one position to another.

Figure 1A:
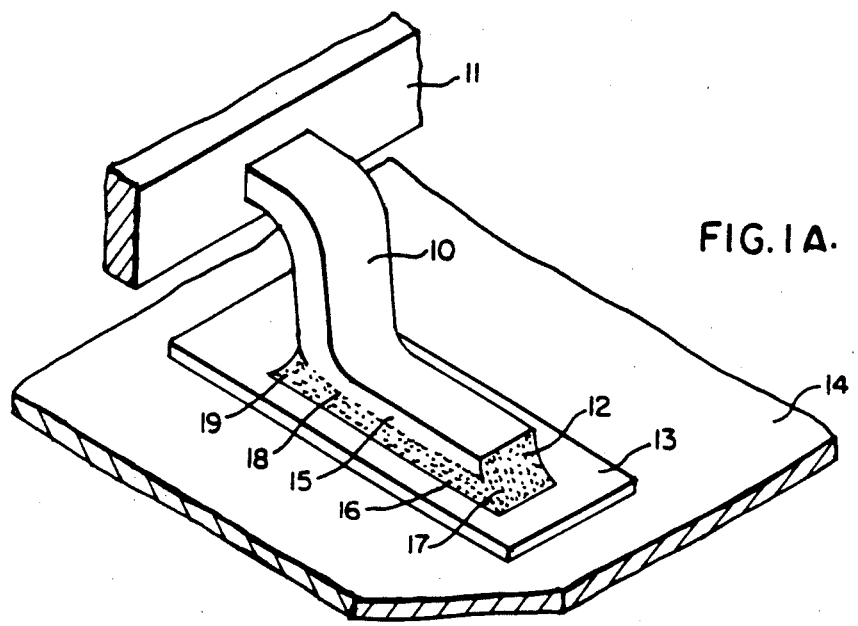
FIGS. 1A, 1B, and 1C show, respectively, a perspective view, a top view, and a cross-sectional elevation view of an enlarged portion of a surface mounted flatpack semiconductor chip attached with solder to a solder pad on a printed circuit board.
Figure 1B:
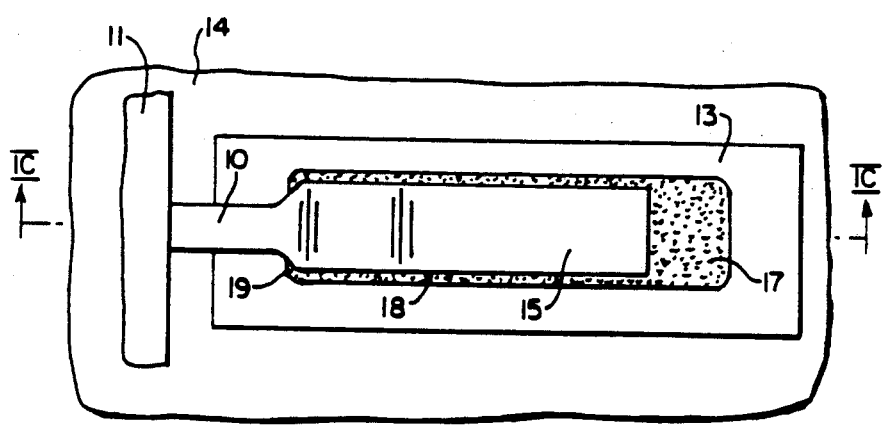
Figure 1C:
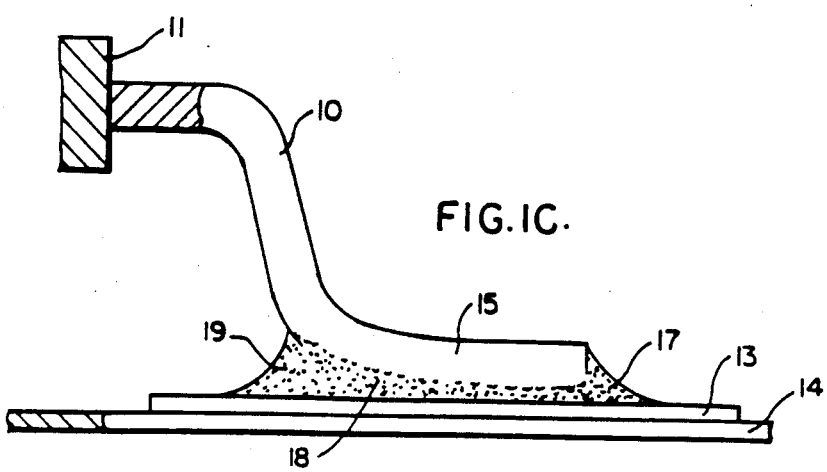

The plurality of penetrations 38 and the center of the camera all are located in a single geometric plane which is coincident to the plane formed by the X-Z axes. For this reason the camera 26 will receive direct reflections from a point light source transmitted through any of the penetrations 38 but only if the reflecting surface is parallel to the Y-axis and situated directly below the camera 26. An exception to this exists because the camera lens and the point light source each have widths such that reflecting surfaces not intersected by the geometric plane or surfaces reflecting at an angle slightly deviating from the plane can still reflect light into the camera lens. As an example of the general case the flatpack chip associated with the solder joint 12 is oriented for inspection in FIG. 5 directly under the camera 26 so that the direction of the lead 15 in FIG. 1B is coincident to the projection of the X-axis directly under the frame 35. Consequently, the data accumulated for the shape of the solder joint will be data associated only with solder along a line similar to that cut by "1C—1C" in FIG. 1B, that is, associated only with the toe portion 17 (FIG. 1C) of the solder joint and not with the shoulder 18 or the heel fillet 19 since the line for inspection does not pass through either of the shoulder portions of the solder joint and the heel fillet is shielded by the lead. Note due to the width of the camera lens and point light source, solder surface slightly away from the line for inspection or surface reflecting light slightly off the geometrical plane defined above will still provide useful data.

Note that while the frame 35 permits identification of only two dimensional shapes, another geometrical configuration such as a fixed hemisphere configuration may be utilized with a compliment of point light sources through penetrations in the hemisphere such that information would be available to determine the three dimensional shape of a solder joint. Also note that in lieu of a hemispherical configuration, the existing frame 35 may be incrementally rotated about the Z-axis shown in FIG. 4 and equivalent data to evaluate a three dimensional solder profile could be acquired. Using a non-rotating frame 35, the solder joint 12 could be rotated beneath the frame 35 for the same results.

Note the camera 26 may be replaced with any similar device having a means of receiving light, such as an array of light responsive transducers, and producing a grid map which indicates the light intensity across the field of view of the camera 26. Each transducer provides an analog signal representing light intensity and this signal must be digitized through a converter before the grid map may be produced. The camera 26 in this embodiment may consist of a JVC type BY-110 Video Camera, which internally converts the analog signal from the transducers in the camera to a digitized signal.

An imaging device 30 (FIG. 4), which is comprised of a thick walled tube 41 houses lenses to magnify the solder joint image for the camera 26 and is connected to the semicircular frame 35. An opening (not shown) through the frame 35 permits an unobstructed path from the upper end of the device 30 through the inside edge of the frame 35. The upper end of the device 30 is attached to the camera 26 through a coupling 43.

The imaging device 30 provides further benefits. For initial positioning of the inspection system over a solder joint and for gross visual inspection, the imaging device 30, with an independent light source 49, uses optical fibers (not shown) inserted in a plurality of circular channels bored longitudinally through the thick walled tube 41 to direct light for illumination of the solder joint. This illumination is not used in lieu of the point light sources but only as a work light. The imaging device may consist of a Scholly type 20.10145 Micro T.V. Probe 145/10 mm. Spacer calibration posts 46 attached to the bottom of the frame 35 permit the system to rest with stability upon a table 47 during set-up. After set-up the posts are retracted so the frame 35 may be controllably moved. One embodiment provides a movable table 47 with a means for translation and rotation such that different portions of the solder joint, such as the shoulder, may be inspected and furthermore a plurality of joints may be inspected through a process of sequential indexing.

The camera 26 in this embodiment contains a $512 \times 512$ array of light responsive transducers such that light from any one of the fibers 39 is reflected from those surfaces so oriented on the specular solder surface to the transducers. Because the solder surface is specular, that is having a smooth surface that reflects light only at the angle of reflection similar to the angle of incidence, only those surfaces that reflect light directly into the lens of the camera 26 will appear in the camera image. Each bright spot in the image, known as a highlight, is the result of a reflection from a single point on the surface of the object. Although the image captured by the camera 26 is that of the entire solder joint and any given point light source illuminates the entire solder joint, only light rays reflected from the solder joint toward the camera 26 lens will generate highlights and excite the transducers. In this manner the array of transducers will reveal those points on the solder joint 12 that have reflected light directly to the camera 26 for a specific point light source and one $512 \times 512$ grid map is generated. This provides enough information to identify the orientation of all of the points on the solder joint surface that show highlights using a specific point light source.

Figure 5:
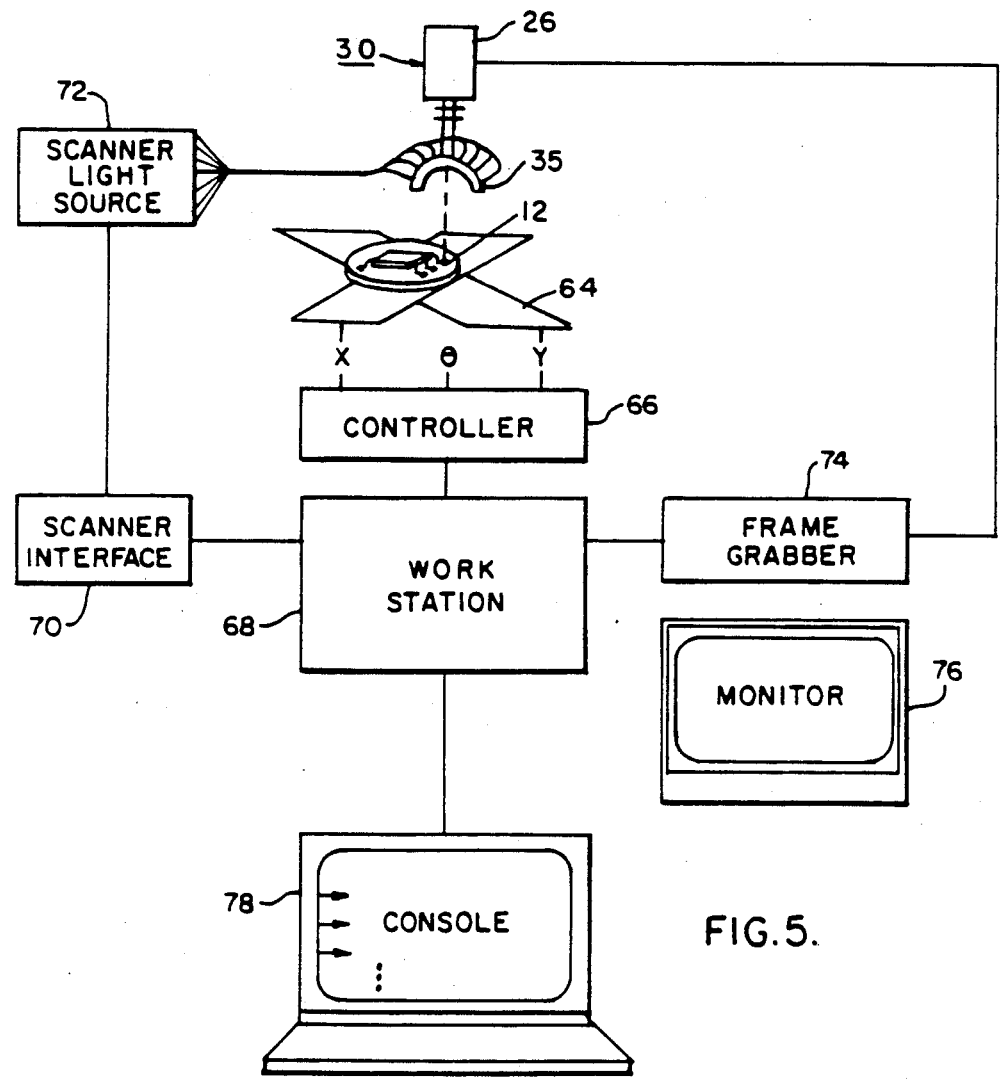
FIG. 5 is a schematic showing the inspection apparatus with supporting equipment.

Because the camera 26 lies in the same plane as that defined by the array of point light sources, only those surfaces with orientations parallel to the Y-axis in FIG. 5 will reflect light directly to the camera 26 from a point light source. For this reason, the capability of the system is limited by the frame 35 so that the current design provides accurate information only along, and very close to (as discussed earlier) a line shown with the plane defined by the point light source locations along the frame 35 and projected onto the solder joint 12. This is similar to the location of the line indicated by the cross-section "1C—1C" arrows in FIG. 1B.

Note also the design in FIG. 4 is limited to acquiring data from reflection from surfaces whose angle in FIG. 2A is less than 45°. For greater than 45°, regardless of the location of the point light source 25 (assuming the source is not below the level of the solder surface), the reflected light would not reflect into the camera 26. This is remedied by the introduction of more cameras. As an example two more cameras could be oriented horizontally on opposite sides of the frame 35, such that one camera would be located approximately where light source 24 is shown and the other camera located directly opposite it. Through the use of plural cameras in conjunction with multiple light sources, the system is capable of determining the shape of any open surface. Just as with the use of a singular camera, each of a plurality of cameras would be at a fixed location and each oriented in a unique direction viewing the solder joint. Occasionally, using multiple cameras, light is reflected from the solder joint to an adjacent solder joint and then rereflected from the solder joint to a camera. This causes erroneous readings, and to minimize this data provided by any given camera may be selectively chosen so that it is representative of an area of point light sources oriented generally in the same direction as the camera.

By sequential illumination of the solder joint 12 using light passing through optical fibers 38 to generate point light sources at different angles around the circumference of the frame 35, a sequence of 512×512 grid maps is provided which indicate those points on the solder joint that reflect light to the camera 26. Each point light source location provides a different pattern of reflected light to the camera 26 identifying the orientation of another set of points on the solder joint 12. Through a collection of grid maps generated using point light sources from a plurality of locations around the frame 35, the orientation of a sufficient number of points on the solder joint may be accumulated so that the solder joint shape may be analyzed. Given the orientation of points on the surface of the solder joint the joint may be reconstructed or the orientation data may be analyzed without the need to reconstruct the surface.

Note the embodiment shown in FIG. 4 will provide enough data for only a two dimensional analysis of the solder joint, whether it be surface reconstruction or solely feature evaluation. The system may be modified so that rather than having point light sources along the radius in a two dimensional path, the frame 35 could be replaced with a hemispherically shaped configuration with associated passages for point light sources so that light could be applied and data collected to reconstruct the three dimensional shape of the solder joint. Just as the design in FIG. 4 would require multiple cameras to receive light that would not reflect to a single camera, so would the design utilizing light point sources arranged in a hemispherically shaped configuration. However, in this design the cameras would not be oriented in a single plane but would be optimally placed at locations on the hemispherically shaped configuration.

Ideally all surfaces on the solder joint 12 Will either completely reflect the light rays or not reflect them at all. In reality a reflection from a curved surface will generate a gradient of intensity. Furthermore, since the solder joint is not a totally specular surface, light will be reflected from all surfaces on the solder joint but the intensity will vary depending on the amount of reflection. In order to simplify interpretation of data provided by the grid maps, which will indicate varying levels of reflected light at different locations, it is necessary to avoid varying levels of light in favor of interpreting the transducers as either "on" or "off". For this reason an intensity threshold was established to screen the data on the grid maps so that only those pixels receiving directly reflected light would be recorded while those transducers receiving dispersed light would not be recorded. Data provided by all of the grid maps from each location of the point light source is converted from an analog to digital signal 50 and input to a microprocessor 52 where the threshold cutoff is enforced and the data is mathematically interpreted to arrive at a solder joint reconstruction.

FIG. 5 is a schematic of the inspection system. The printed circuit board with an attached chip and solder joint 12 rest on a movable table 64. The movable table 64 is indexed using a controller 66 operated by a main workstation 68. Once the solder joint 12 is in position under the imaging device 30, a signal is sent from the workstation 68 via the scanner interface 70 to illuminate with the point light source one of the optical fibers 39 in the imaging device 30 through the scanner light source 72. The scanning device 40 in FIG. 4 is comprised of the scanner interface 70 and the scanner light source 72 of FIG. 5. With an optical fiber now illuminating the solder joint 12 surface, the camera in the imaging device 30 receives an image of the light reflected from the specular solder joint 12 surface. The reflected light excites the array of transducers (512×512) in the camera so that a frame grabber 74 records the pattern of light indicated by the pixels. Typically each transducer generates a small voltage and the voltage is recorded. This information is sent to the workstation 68 for display on a monitor 76 and for further processing 78. The further processing includes binarizing the transducer values based on a threshold discussed earlier and then either utilizing features already known about solder joints coupled with curve fitting techniques to generate a profile of the solder joint surface and then evaluate certain features to determine the solder joint integrity or solely evaluating the solder joint surface orientation without surface reconstruction.

Figure 6:
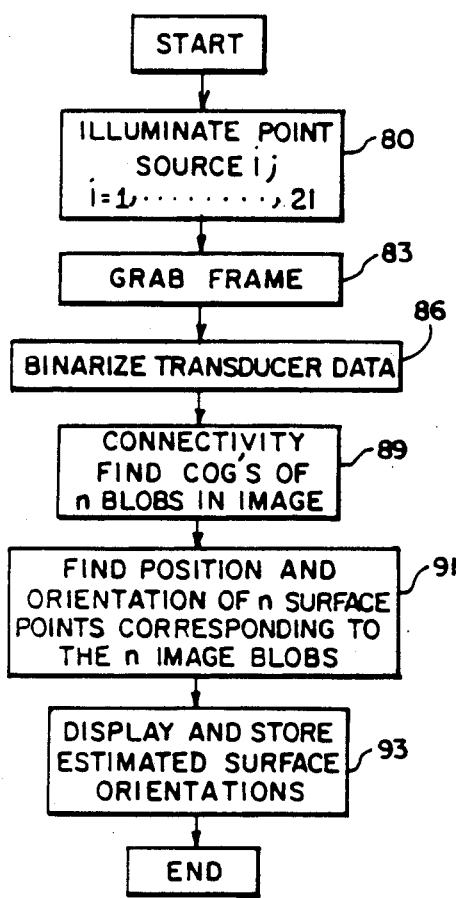
FIG. 6 is the flow chart with blocks representing functional operations for determination of the solder joint shape.

FIG. 6 illustrates a flow chart for the measurement of the solder joint surfaces and a determination of estimated surface orientations for surface reconstruction. With the first point source illuminated 80, the 512×512 transducer camera image is processed through a frame grabber 83, which digitizes the 512×512 array (grid map) and assigns a value to each element in the array representing light intensity at that element. This array is then converted into a binary form 86 using a threshold intensity value such that all elements in the array will be deemed either off or on depending on whether or not these individual elements meet or exceed the threshold intensity value.

With a binary array, the areas of directly reflected light may be identified and used to define areas of the solder joint oriented in the same plane. Given a group of adjacent transducers indicating directly reflected light from a given point light source, it is not necessary to separately calculate the orientation of each point on the solder surface. Instead an equivalent center of light is calculated based on the location of the reflecting surfaces. Each point on the surface that reflects is referred to as a blob and the center of gravity (COG), actually the center of light, is calculated 89 with this information on clusters of blob concentration. With this information, the surface orientation of some portions of the solder joint is known 91. This utilization of the center of light is especially helpful in surface reconstruction; however, when the surface orientation is analyzed directly, such as through the utilization of Extended Gaussian Images, this approach is not as helpful and may be avoided. A partial map is then displayed and stored 93. Moving the point source to the second position 80, another 512×512 array of light intensity values is generated and again this information is processed to generate another map representing surface orientations. With each point source illumination, a new set of data is accumulated and processed so that after the last point source data has been accumulated, a series of grid maps exist which together provide a series of arrays representing the surface orientation of local areas across the face of the soldered joint.

Note this measurement technique does not measure the absolute height of points on the surface of the soldered joint, but measures only the surface orientation. Furthermore due to a deliberate deficiency of data points if surface reconstruction is desired the surface of the soldered joint must be reconstructed using the estimated surface orientations at different points on the surface and curve fitting techniques must be utilized to generate a continuous solder joint profile. Note that with a greater number of point light source locations, a more comprehensive collection of data could be acquired so there may no longer be a deficiency of data. Increased point source locations however would generate an increased amount of data that would require additional processing thereby slowing the feature identification process. For this reason, a relatively few number of point light sources are used and the information available is maximized utilizing curve fitting techniques when reconstruction is desired or utilizing analysis techniques that utilize surface features and do not require surface reconstruction.

Given the orientation of a number of points on the surface of a solder joint, the acceptability of the solder joint may be determined in at least one of two ways. The surface may be reconstructed and features extracted for comparison with acceptable features or the surface orientation may be used to generate an Extended Gaussian Image which may be analyzed.

As indicated earlier, multiple point light sources may be simultaneously illuminated.

The inspection system may use a binary coding scheme to expedite the scanning of point sources. For a large number of point sources, coded scanning is far more efficient than individual sequential scanning. For example, if each frame grab takes sixty milliseconds than individual sequential scanning of one hundred twenty-seven point sources, the number which could exist for the hemispherically shaped configuration of sources, then sequential scanning would take a total of over seven seconds. Point source scanning using binary coding would be beneficial. As an example, using only seven point sources, only three scans are necessary.

TABLE 1

| POINT SOURCE | BINARY VALUE | SCAN NUMBER 3 | 2 | 1 |
|---|---|---|---|---|
| 1 | 001 | off | off | on |
| 2 | 010 | off | on | off |
| 3 | 011 | off | on | on |
| 4 | 100 | on | off | off |
| 5 | 101 | on | off | on |
| 6 | 110 | on | on | off |
| 7 | 111 | on | on | on |

As seen in Table 1, the source numbers are converted into their corresponding binary code. The numbers from 1 through 7 can each be uniquely expressed in binary form by using three bits, such as those shown in Table 1. For the first scan, all point sources that have a high bit in the least significant bit are turned on and the remaining sources are turned off. An image of the surface is grabbed into the frame buffer of the computer and converted to a binary image using a threshold. The binary image is comprised of an array. A "1" in the binary image corresponds to a highlight and "0" otherwise. The binary image corresponding to Scan (1), the first scan, is Binary Image (1). In a similar manner, the Binary Image (2) and Binary Image (3) are obtained for Scan (2) and Scan (3), respectively. By reading the contents of the same pixel location (i, j) in all three binary image arrays, a three bit pattern is obtained, such as (, 1, 0, 1) for a pixel highlighted by source 5. The assumption is made that only a single point source can generate a highlight at any particular point on the surface due to high surface specularity. Therefore, the bit pattern (1, 0, 1) in the binary images could result only if the point (i, j) on the object surface represented by the pixel reflected light from point source 5 into the image. The surface orientation at point (i, j) is computed by using the source direction of point source 5 and the viewing direction. Generalizing this example ($2^N-1$) point sources can be scanned in N frame grabs. In a system with one hundred twenty-seven point sources, only seven frame grabs are required. This method of binary coding may be extended to larger numbers of point sources.

EVALUATION BY RECONSTRUCTION OF THE SOLDER JOINT

Figure 7A:
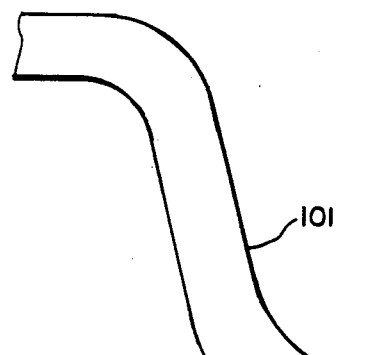
FIGS. 7A, 7B, 7C and 7D show a profile of a typical solder joint and a variety of profiles that would flag the joint as defective.
Figure 7A:
Figure 7B:
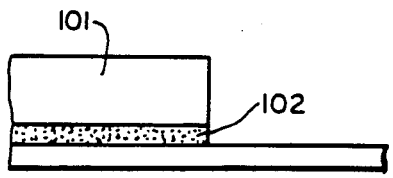
Figure 7C:
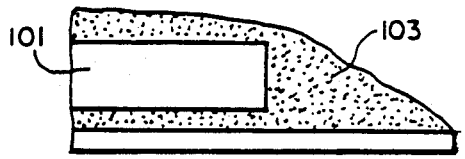
Figure 7D:
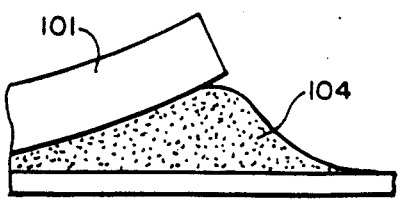

One embodiment of this invention evaluates the acceptability of a solder joint by reconstructing the surface of the joint and then evaluating features on the reconstructed joint surface. Just as a quality solder joint shows characteristic features, so does a defective joint. FIG. 7A shows the profile of an acceptable toe portion 100 of the solder joint relative to the lead 101 from a chip. Note the quality of the solder joint overall depends on the shoulder portion and the heel fillet as well as the toe portion. Similar profiles may be generated for these other portions and the inspection apparatus may be oriented to extract shape features of these areas as well. FIGS. 7B, 7C and 7D show a series of deviations in the toe region that may result in an unacceptable solder joint. FIG. 7B shows a "sharp toe" deviation 102 that depending on the severity, may result in an unacceptable solder joint caused by an insufficient amount of solder. FIGS. 7C and 7D show a "high toe" deviation 103 and a "toe up" deviation 104, respectively. A "high toe" deviation is indicative of excessive solder on the lead while a "toe up" deviation indicates a faulty chip lead that is not bonded with an adequate solder joint. While a multitude of potentially defective shapes exist, these figures provide a representative sampling and valid generalizations may be made based on them. The reconstructed shape of the toe portion of the solder joint is compared to the different acceptable and unacceptable solder shapes to determine the quality of the solder joint at the toe. Although not shown in FIGS. 7B, 7C and 7D, various defect flags may be defined for other sections of the solder joint, such as the shoulder and the heel fillet, to highlight common flaws such that any deviation may be identified.

After the joint shape has been determined and any deviations identified, it is necessary to evaluate the deviations to determine whether or not they are sufficient to deem the joint unacceptable. A well founded determination of the solder joint integrity must be based on more than information about the toe region of the solder joint. With similar data about the acceptable and unacceptable features of the shoulder portion of the joint coupled with shape information acquired using the apparatus in this invention, a decision tree may be established to classify the solder joint.

Figure 8:
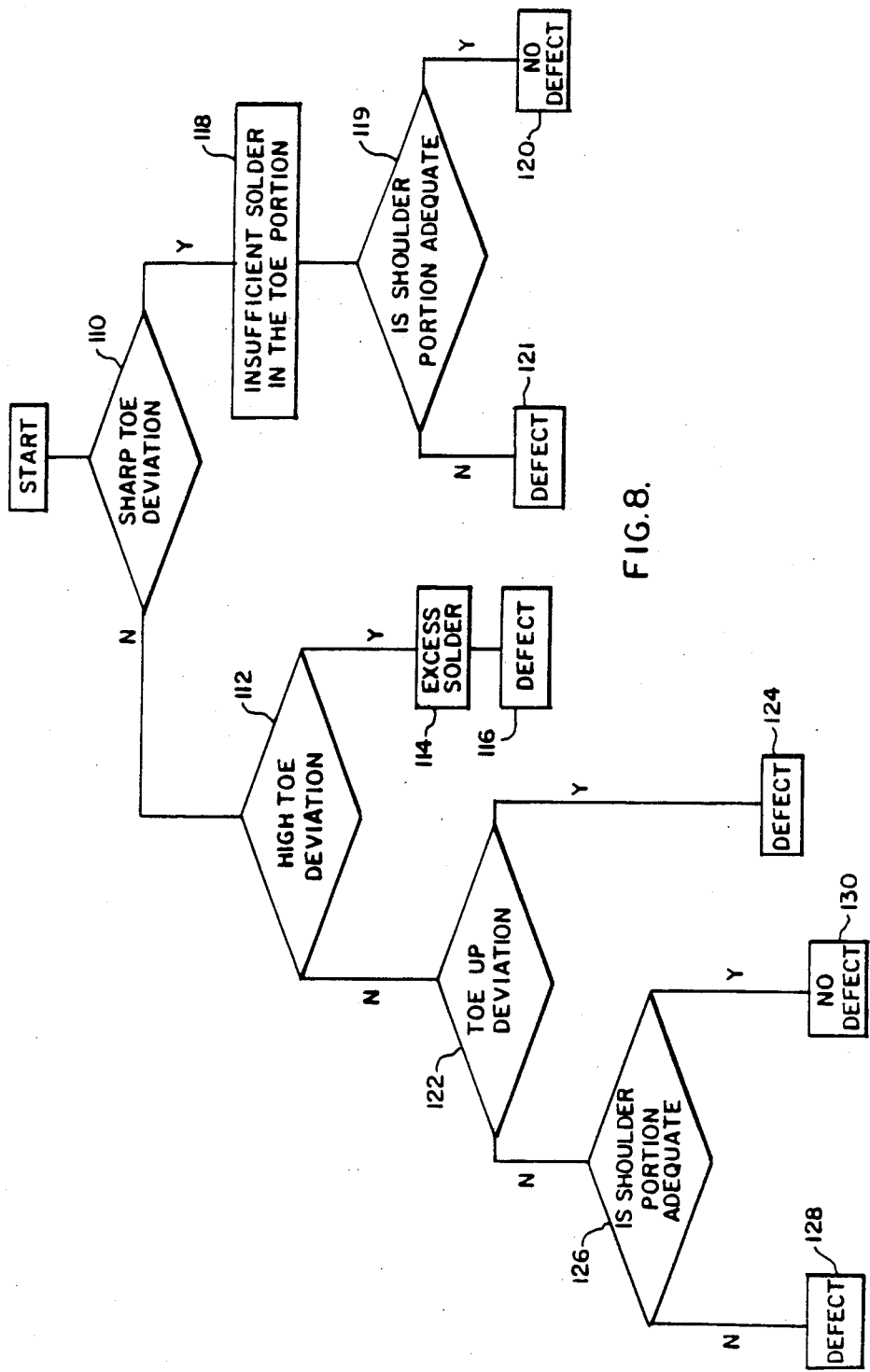
FIG. 8 illustrates a possible decision tree used in software for a rule-based computer program to evaluate the quality of a solder joint.

FIG. 8 illustrates a decision tree to classify the solder joint based on information from the toe region and the shoulder region of the solder joint. While the focus of FIG. 8 is the toe region of the solder joint, the decision tree is indicative of the approach used and provides a general overview for evaluating the solder joint acceptability. As an example, assume that after inspection of a solder joint using the inspection apparatus of this invention the toe portion was deemed to have a "high toe" as shown in 103 of FIG. 7C. Following the path presented in the decision tree, the toe portion would not be categorized as a "sharp toe" deviation 110, but would be under the "high toe" deviation 112. For this reason the deviation would fall into the "excess solder" category 114. Based on the concern that excessive solder will touch an adjacent lead resulting in a short circuit, generally the "excess solder" category is considered a defect 116 without further inquiry. On the other hand a "sharp toe" deviation 110, although indicative of an insufficient amount of solder at the toe 118 of the solder joint, may be offset 119 by the existence of adequate solder on the shoulder of the chip lead such that the joint is acceptable 120. Without adequate solder on the shoulder, the joint would be defective 121. Another classification addressed in the decision tree is that of the "toe up" deviation 122. A "toe up" deviation 122 essentially identifies a defective chip lead but still would involve a defective solder joint and therefore this deviation is considered a defect 124. Finally, if no deviations are identified in the toe portion of the solder joint, then the shoulder portion must still be checked 126 and depending on the adequacy of the solder on the shoulder, the joint may be acceptable 128 or defective 130.

While FIG. 8 is focussed on evaluating the toe portion of the solder joint and merely mentions evaluation of the shoulder portion, the evaluation of the shoulder portion would be categorized in a similar manner using typical deviations. Similar categorization would also be done for the heel fillet of the solder joint. Considering this, it is easier to envision how the decision tree in FIG. 8 would be expanded for a more detailed evaluation of a solder joint. FIG. 8 illustrates that while a combination of deviations will likely result in an unacceptable joint, often times a singular marginal deviation may not be sufficient to deem the entire joint unacceptable. Furthermore, the decision tree illustrated in FIG. 8 may be included in a computer software program such that the entire inspection process may be automated.

While the information in FIGS. 7 and 8 may be useful for a human inspector, this information is critical for the current inspection system described in this invention. As mentioned earlier the shape features of acceptable and unacceptable solder joints are known. The process for determining the solder joint profile has been explained and automated as described. The unacceptable joint shape features, or defects, are now stored in data so that the shape features of any joint inspected by this system may be compared with defective shape features. Since singular defects or certain combinations of singular defects result in the entire joint being deemed unacceptable, a rule-based computer program utilizes the decision tree presented in FIG. 8 to determine whether or not a given joint is acceptable. Furthermore the computer program algorithm may utilize the acquired information to generate a level of confidence for each diagnosis of solder joint acceptability.

The solder joint may also be evaluated without the necessity of reconstructing the joint shape. The orientation data that could be used to reconstruct the solder joints is valuable in itself.

EVALUATION BY THE GENERATION AND ANALYSIS OF AN EXTENDED GAUSSIAN IMAGE FOR THE SOLDER JOINT

Figure 9:
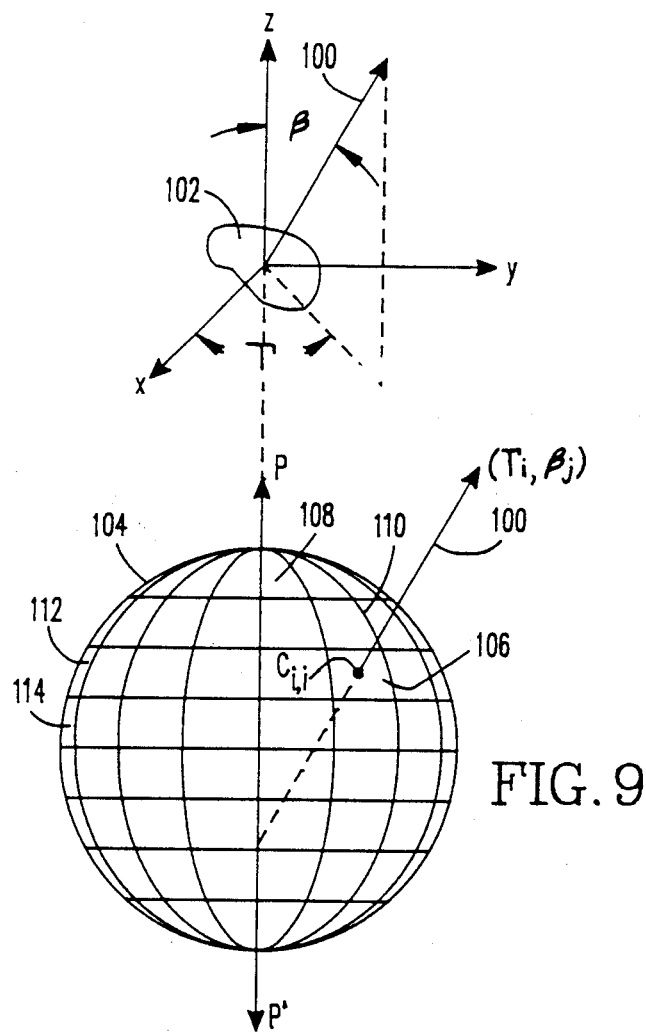
FIG. 9 shows one orientation point of an object mapped onto a Gaussian sphere to describe the Extended Gaussian Image of an object.

As mentioned, it is possible to evaluate the solder joint acceptability without the need to reconstruct the entire solder joint surface through the use of the Extended Gaussian Images. An Extended Gaussian Image (EGI) is an image generated strictly based on surface orientations of an object such that any point on the object is mapped onto the surface of a sphere, known as a Gaussian sphere, at a location on the sphere which corresponds to the object surface orientation of that point on the object. Using the known surface orientations at a number of points on the surface of the solder joint, an EGI of the solder joint may be generated. From FIG. 9, a unit surface normal vector 100 representing the surface orientation at a point on an object 102 surface can be mapped to a Gaussian sphere 104 so that the tail of the normal vector 100 intersects the center of the sphere, and the head of the normal vector 100 lies on the surface of this sphere 104. Note that FIG. 9 is slightly modified for clarity to show the vector 100 outside of the sphere 104. The vector 100 in FIG. 9 has an azimuth angle $\beta$ and a colatitude angle $\Gamma$ to identify a unique position upon the Gaussian sphere 104.

The sphere 104 and each point on it corresponds to a unique surface orientation. Generally, the surface of the sphere 104 is divided into cells 106 with each cell corresponding to a small range of orientations. A longitude/latitude tessellation, which is the pattern that describes the cells 106 on the sphere 104, was selected because for the function of solder joint inspection, this tessellation provided good results. However, other tessellations might be used. Given an object having surfaces oriented in many directions, as the object 102 shown in FIG. 9 may have, an EGI of that object is obtained by placing at each cell 106 on the sphere 104 a fictitious "mass" proportional to the number of points on the surface of the object that have the orientation at that cell 106 on the sphere 104. Given a number of points all orientations with a specified range fall within a single cell on the EGI and therefore contribute to the "mass" of that cell. All points in the cell 106 of the Gaussian sphere 104 are assumed to have the same spherical angles $(\Gamma_i, \beta_j)$ and also all cells with the same azimuth angle are assumed to have equal cell areas.

Figure 10B:
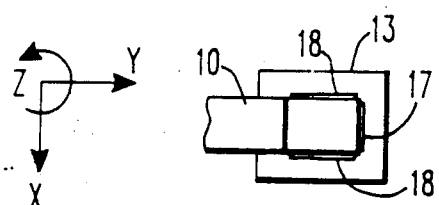
FIGS. 10A, 10B and 10C show the section of a solder joint with insufficient solder of a lead to a solder pad, the top view of the solder joint and the Extended Gaussian Image of the solder joint, respectively.
Figure 10A:
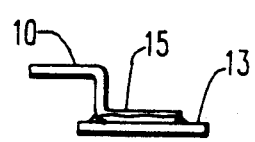
Figure 10C:
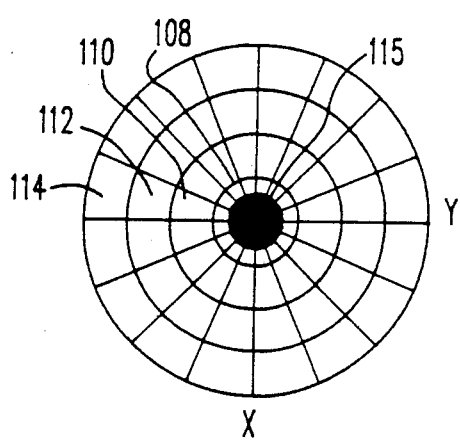
Figure 11B:
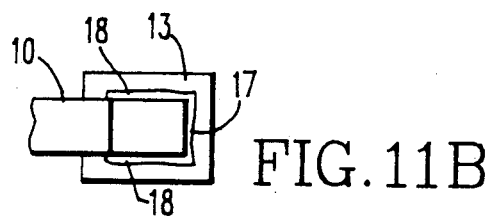
FIGS. 11A, 11B and 11C show the section of a solder joint with adequate solder of a lead to a solder pad, the top view of the solder joint and the Extended Gaussian Image of the solder joint, respectively.
Figure 11A:
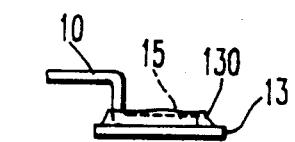
Figure 11C:
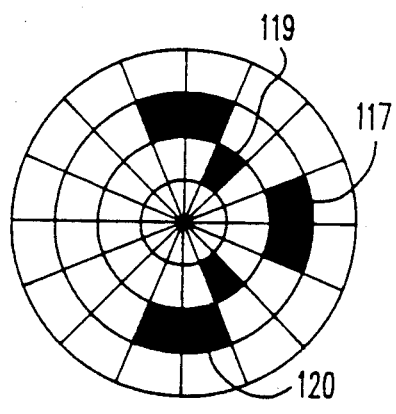
Figure 12A:
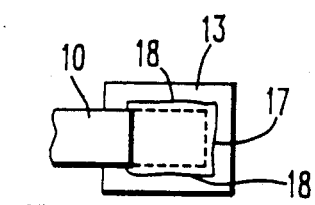
FIGS. 12A, 12B and 12C show the section of a solder joint with excessive solder of a lead to a solder pad, the top view of the solder joint and the Extended Gaussian Image of the solder joint, respectively.
Figure 12B:
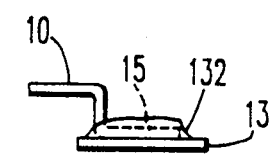
Figure 12C:
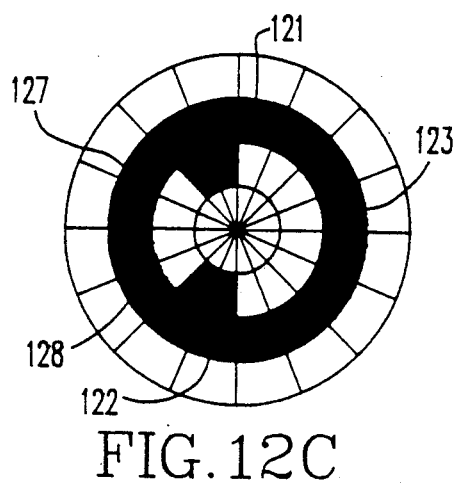

FIGS. 10, 11 and 12 are presented as examples of typical solder joints. The "A" figures illustrate a top view of a solder joint on a typical chip lead 10 on a solder pad 13. The "B" figures illustrate a cross-section "B—B" of the solder joint with the chip lead 10 and the solder pad 13. The "C" figures illustrate the representative EGIs for the solder joints shown in the "A" and "B" figures. In FIGS. 10C, 11C and 12C the EGIs are represented differently than as shown on the unit sphere of FIG. 9. In these figures the EGI is shown as a projection of the top half of the sphere as viewed along the z axis. The four concentric rings 108, 110, 112 and 114 shown in FIGS. 10C, 11C and 12C represent rings 108, 110, 112 and 114 of FIG. 9. The diametric lines in conjunction with the rings define cells.

Note that in determining the "mass" to be assigned to each cell in the EGI, the projected surface area of a surface element depends on the inclination of the surface. A surface that is steeply inclined is foreshortened and appears smaller than it would if it were viewed head on. For this reason, the projected size of each cell in FIGS. 10C, 11C and 12C is adjusted accordingly. As mentioned, for the solder joints in FIGS. 10, 11 and 12 the EGIs presented in FIGS. 10C, 11C and 12C are those images that would be observed from a view along the z axis shown in FIG. 9. Furthermore, note that the representative "mass" in the cells in FIGS. 10C, 11C and 12C is solid. In actuality the "mass" may be any shade, thereby illustrating the density of the "mass" in a cell.

FIGS. 10A and 10B show an example of an unacceptable solder joint in which there is not an adequate amount of solder. When solder is present, its highly specular surface will provide strong reflections which are used to determine orientation. Absent these strong reflections, other reflections such as those from the chip lead surface will provide the only information available. It is this information that will be analyzed to determine surface orientation. Because of this, the surface orientations will be provided from the lead 10 surface in the foot 15 region. Since the surface of the foot is essentially planar, all of the orientation vectors will be aligned with the z axis. This is illustrated in the representative EGI of this arrangement. The black dot 115 falls within ring 108 and illustrates that all of the orientations of the lead 10 occur approximately in the same direction. Consistent with the sphere found in FIG. 9 this reflection would essentially correspond to the z axis which is represented by ring 108.

FIGS. 11A and 11B, on the other hand, show a lead 10 connected to a pad 13 with adequate solder 130 representative of an acceptable solder joint. In this instance the foot 15 of the lead 10 does not provide the primary reflection since now solder 130 provides a specular surface upon which reflections may be received. A typical example of an adequate solder arrangement would involve the presence of solder 130 along each of the shoulders 18 and at the toe 17 of the solder joint. Generally the toe 17 of the solder joint would provide the EGI in FIG. 11C with a concentration of orientations typical to that shown by the concentration 117. Furthermore, the solder 130 along the shoulders 18 would be indicated by the concentrations shown as 119 and 120. Note that there is a certain symmetrical pattern in the EGI of at least this type of adequate solder joint.

FIGS. 12A and 12B show a lead 10 attached to a pad 13 with excessive solder representative of an unacceptable solder joint. Here the solder 132 is excessive enough to generate a shape which approximates a dome. For this reason while in the EGI of FIG. 12C there will be areas of concentration 121 and 122 representative of the shoulder 18 areas of the solder joint, and furthermore an area 123 of concentration representative of the toe 17 of the solder joint, there will be still more areas of concentration which will indicate the excess solder 132 on the solder joint. As might be expected, the surface of the excessive solder 132 has orientations in directions not normally associated with acceptable solder joints. This is illustrated by the areas of concentration 127 and 128 which corresponds to the solder resting on top of the foot 15 near the bend in the lead 10. While the three examples shown in FIGS. 10, 11 and 12 provide only general approximations to illustrate the application of the Extend Gaussian Images to specular solder joints, the information provided using EGIs may be analyzed to provide a still more detailed analysis.

Given an EGI for a solder joint, the EGI may be compared to EGIs for acceptable solder joints. Considerable attention has been given to recognizing three dimensional objects by matching their EGIs. However, in applications such as solder inspection it is not possible to define a single model that represents a good solder joint. Since many solder joints of different shapes may be classified as joints of good quality. Generating all of the possible models that qualify as acceptable solder joints would involve a great deal of computation.

An alternative approach to this identifies solder defects by extracting local and global features from the EGI representing the solder joint. These features relate well to the physical shape of the solder joint. Global features which are representative of the overall EGI are determined by using the properties of the EGI which and are computed over the entire visible hemisphere of the EGI, such as that hemisphere shown in FIGS. 10C, 11C and 12C. Note that FIGS. 10C, 11C and 12C actually illustrate only the top half of the Gaussian sphere since no meaningful data exists for the lower half of the sphere.

Typical global features of the EGI may be calculated and provide a distinct identification for a given EGI. Such global features include the center of "mass" which is defined with coordinates $(X_c, Y_c, Z_c)$ as the center of orientation concentrations provided with respect to the x, y and z axis. The calculation is similar to the calculation for calculating the center of mass of a sphere having all of its mass along the surface. Furthermore an area ratio, $Z_c$, which is the ratio of the area, $A_{cs}$, of an EGI projection of the existing solder surface to the overall EGI area, $A_s$, may also provide valuable information. A third global feature is the distribution of the "mass" over a set of rings of the EGI relative to the overall "mass" of the entire EGI. This value is called the sample mean, $\phi_m$, of the azimuth component of the surface orientation.

Figure 13:
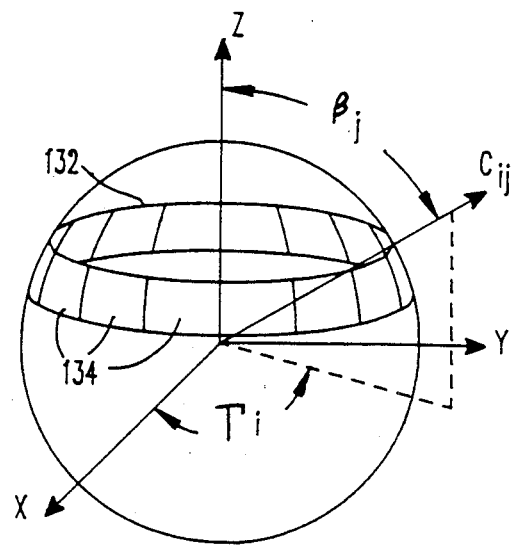
FIG. 13 illustrates a Gaussian sphere with one ring highlighted to evaluate local features of an Extended Gaussian Image.

On the other hand, local features are used to describe subtleties in the shape of an object. FIG. 13 illustrates a Gaussian sphere 130 with a ring 132 highlighted about the circumference of the sphere 130. Just as in FIG. 9, the unit surface normal vector 100 is again shown. One such group of local features focus upon the rings of the sphere. As an example, local features are computed over a ring 132 on the EGI where a ring is constituted by cells 134 that have the same azimuth angle $\beta$. Realizing that the EGI is comprised of a series of many rings 132, the "strength", $S_j$, of an individual ring may be evaluated as the total "mass" contained within the ring itself. This "mass" may then be compared with the "mass" of other rings to provide a unique "strength", $S_j$, value of the image.

Furthermore, just as the entire EGI has a center of "mass" so does each ring 132 and this may also be used for analysis. In this manner a second local feature, the ring center of "mass", exists. A collection of center of "mass" values at each ring provides a unique identification for a specific EGI. Other local features may also be calculated such as the homogeneity, $H_j$, of the "mass" in each cell of a given ring. This value may be compared to that value for other rings.

Given a series of values for global and local features of an EGI representing a solder joint, it is possible to select at least one set of features for the task of classifying a solder joint. Feature values from a representative set of acceptable solder joints are calculated and used as acceptable values and other solder joint features are compared to these. However, a group of different feature values, as opposed to a single feature, must be considered together before an evaluation of a solder joint may be made.

Figure 14:
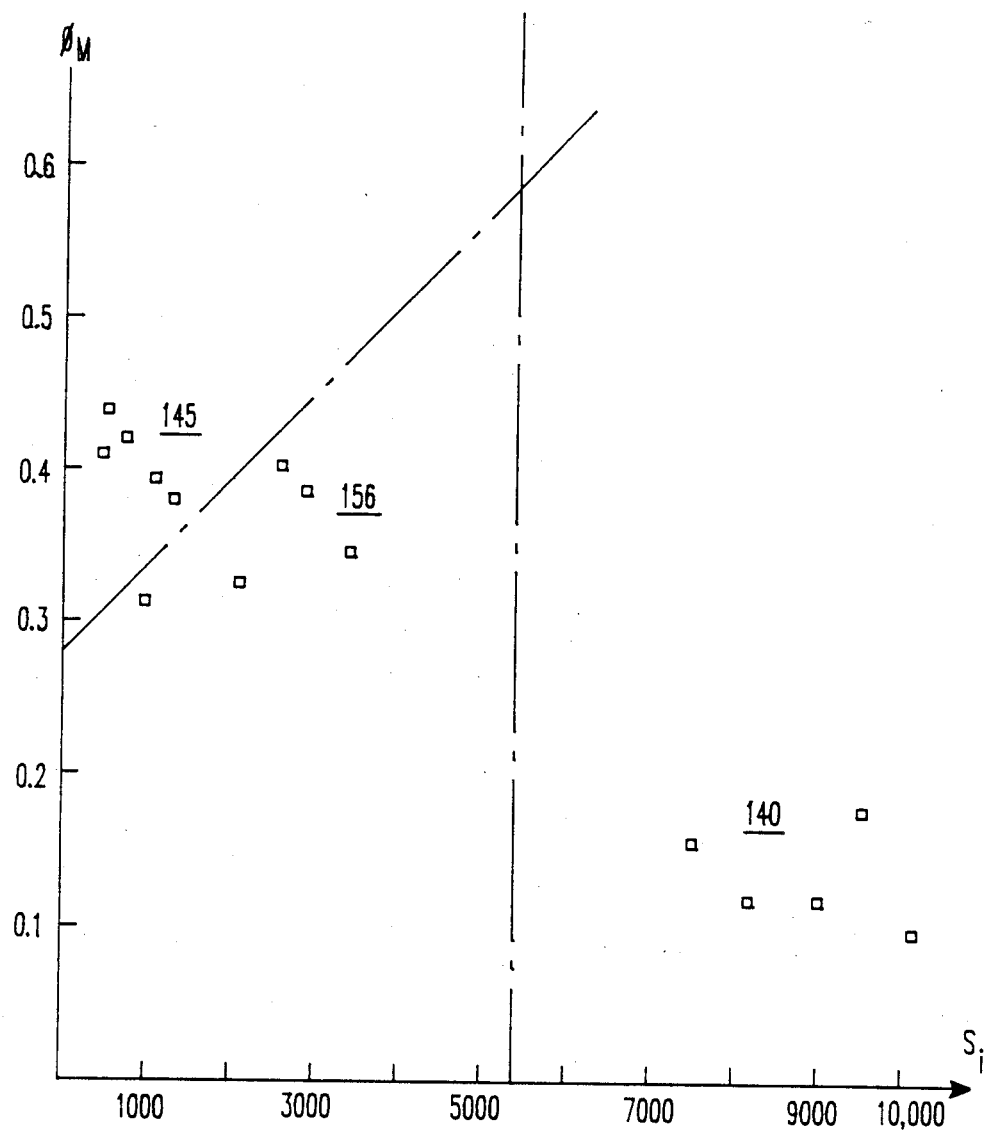
FIG. 14 illustrates one possible graph to evaluate solder joints based on classification through Extended Gaussian Image features.

FIG. 14 shows a graph of one such grouping for solder joint evaluation. The local feature of strength, $S_j$, is measured along the axis of abscissae and the local feature of sample mean, $\phi_m$, is measured along the axis of ordinate. Using sample unacceptable solder joints with insufficient solder, EGIs were generated and $S_j$ vs. $\phi_m$ was plotted. These points 140 tended to cluster. The same was done using unacceptable solder joints having excess solder and these points 145 also tended to cluster but in an entirely different region on the graph. The same procedure was followed with acceptable solder joints and these points 150 also clustered. Based on this clustering, boundaries P and Q were defined and any $S_j$ vs. $\phi_m$ values calculated for a solder joint within these boundaries were considered representative of acceptable solder joints.

Note the system is not limited to inspection of only surface mounted flatpack semiconductor chip solder joints but may be utilized as an inspection system for any type of solder joints as long as information about the shape of the specific solder joint with acceptable and unacceptable solder joint features are known. Finally, this system may be modified slightly for inspection of many other small items having specular surfaces, such as polished machine parts.

The description of this invention is intended to be merely exemplary and not circumscriptive of the invention as it is claimed below. The invention, thus, may be modified by those skilled in the art and yet be within the scope of such claims.

We claim:

1. A method for inspecting an object having a specular surface comprising the steps of:
   (a) projecting sequentially toward the object the light from each of a plurality of point light sources which are arranged in a fixed configuration about a common site at which the object is placed for inspection;
   (b) viewing the object at the common site to detect light patterns caused by the reflections of light of each point light source from the object surface;
   (c) interpreting the light patterns to determine the surface orientation of points on the object surface; and
   (d) evaluating the object surface based on the surface orientation of points on the object surface by (i) mapping, with knowledge of the object surface orientation, the unit surface normal at each point on the object onto a Gaussian sphere to generate an Extended Gaussian image of the object and (ii) comparing the object Extended Gaussian image with the Extended Gaussian image of at least one acceptable object.

2. The method as defined in claim 1 wherein the comparing step is comprised of (i) calculating a variety of global and local features for the object Extended Gaussian image and (ii) comparing the variety of global and local features for the object Extended Gaussian image with those features associated with acceptable objects.

3. The method as defined in claim 1 wherein the projecting step utilizes light from a plurality of light sources which are arranged in a fixed arcuate two-dimensional configuration about a common site at which the object is placed for inspection.

4. The method as defined in claim 1 wherein the projecting step utilizes light from a plurality of light sources which are arranged in a fixed hemispherical configuration about a common site at which the object is placed for inspection.

5. The method as defined in claim 1 wherein viewing the object at the common site is done from a single direction at a fixed location.

6. The method as defined in claim 1 wherein viewing the object at the common site is done from a different singular direction at each of a plurality of fixed locations.

7. The method as defined in claim 1 wherein the interpreting step is comprised of converting an analog signal representing intensity into a digital signal and utilizing a threshold value to eliminate signals produced by light not directly reflected from the object surface, thereby producing a series of binary signals indicating whether or not a surface reflects light from specific point light sources.

8. The method as defined in claim 1 wherein the projecting step is comprised of sequentially projecting toward the object specified sets of point light sources and wherein the interpreting step comprises utilizing binary coding methodology to determine surface orientation.

9. A method for inspecting an object having a specular surface comprising the steps of:
   (a) projecting sequentially toward the object the light from each of a plurality of point light sources which are arranged in a fixed hemispherical configuration about a common site at which the object is placed for inspection;
   (b) viewing the object at the common site to detect patterns caused by the reflections of light of each point light source from the object surface wherein viewing the object at the common site is done from a single direction at a fixed location;
   (c) interpreting the light patterns to determine the surface orientation of points on the object surface; and
   (d) evaluating the object surface based on the surface orientation of points on the object surface wherein evaluating is comprised of (i) mapping, with knowledge of the object surface orientation, the unit surface normal at each point on the object onto a Gaussian sphere to generate an Extended Gaussian Image of the object, (ii) calculating a variety of global and local features for the object Extended Gaussian Image and (iii) comparing the variety of global and local features for the object Extended Gaussian Image with those features associated with acceptable objects.

10. A non-contact inspection apparatus for inspecting an object having a specular surface comprising:
    (a) an array of point light sources spaced apart from one another in a fixed configuration about a common site at which the object is placed for inspection;
    (b) means for sequentially activating each of the point light sources for emitting light toward the object;
    (c) means for viewing the object at the common site to detect light patterns caused by the reflections of light of each point light source from the object surface;
    (d) means for interpreting the light patterns to determine the surface orientation of points on the object; and
    (e) means for evaluating the object surface based on the surface orientation of points on the object surface comprised of (i) mapping, with knowledge of the object surface orientation, the unit surface normal at each point on the object onto a Gaussian sphere to generate an Extended Gaussian image of the object and (ii) comparing the object Extended Gaussian image with the Extended Gaussian image of at least one acceptable object.

11. The apparatus as defined in claim 10 wherein the comparing step is comprised of (i) calculating a variety of global and local features for the object Extended Gaussian image and (ii) comparing the variety of global and local features for the object Extended Gaussian image with those features associated with acceptable objects.

12. The apparatus as defined in claim 10 wherein the array is comprised of point light sources spaced apart from one another in a fixed arcuate two-dimensional configuration.

13. The apparatus as defined in claim 10 wherein the array is comprised of point light sources spaced apart from one another in a fixed hemispherical configuration.

14. The apparatus as defined in claim 10 wherein the means for viewing the object at the common site for detecting light patterns is comprised of an array of light responsive transducers oriented toward the object in a single direction at a fixed location.

15. The apparatus as defined in claim 10 wherein the means for viewing the object at the common site for detecting light patterns is comprised of an array of light responsive transducers oriented toward the object from a different singular direction at each of a plurality of fixed locations.

16. A non-contact inspection apparatus for inspecting an object having a specular surface comprising:
  (a) an array of point light sources spaced apart from one another in a fixed configuration about a common site at which the object is placed for inspection wherein the array is comprised of point light sources spaced apart from one another in a fixed hemispherical configuration;
  (b) means for sequentially activating each of the point light sources for emitting light toward the object;
  (c) means for viewing the object at the common site to detect light patterns caused by the reflections of light of each point light source from the object surface wherein the means for viewing the object at the common site for detecting light patterns is comprised of an array of light responsive transducers oriented toward the object from a different singular direction at each of a plurality of fixed locations;
  (d) means for interpreting the light patterns to determine the surface orientation of points on the object; and
  (e) means for evaluating the object surface based on the surface orientation of points on the object surface wherein the means for evaluating is comprised of (i) mapping, with knowledge of the object surface orientation, the unit surface normal at each point on the object onto a Gaussian sphere to generate an Extended Gaussian Image of the object, (ii) calculating a variety of global and local features for the object Extended Gaussian Image and (iii) comparing the variety of global and local features for the object Extended Gaussian Image with those features associated with acceptable objects.

* * * * *